US006802848B2

(12) United States Patent
Anderson et al.

(10) Patent No.: US 6,802,848 B2
(45) Date of Patent: Oct. 12, 2004

(54) SURGICAL CLIP WITH ADJUSTABLE BIASING FORCE

(75) Inventors: Russell J. Anderson, Union City, CA (US); Karrie L. Sturtz, Campbell, CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 436 days.

(21) Appl. No.: 10/097,088

(22) Filed: Mar. 12, 2002

(65) Prior Publication Data

US 2003/0176879 A1 Sep. 18, 2003

(51) Int. Cl.[7] .............................................. A61B 17/08
(52) U.S. Cl. ...................... 606/157; 606/158; 606/151; 24/523
(58) Field of Search .................................. 606/157, 158, 606/151, 216, 217, 221, 213; 24/523, 525, 527, 528

(56) References Cited

U.S. PATENT DOCUMENTS

| 3,326,217 | A |   | 6/1967  | Kerr |
| 3,509,882 | A |   | 5/1970  | Blake |
| 3,510,923 | A | * | 5/1970  | Blake .......................... 606/158 |
| 4,106,508 | A |   | 8/1978  | Berlin |
| 4,337,774 | A |   | 7/1982  | Perlin |
| 4,815,466 | A |   | 3/1989  | Perlin |
| 4,817,604 | A |   | 4/1989  | Smith, III |
| 4,931,058 | A |   | 6/1990  | Cooper |
| 5,653,720 | A |   | 8/1997  | Johnson et al. |
| 5,984,934 | A |   | 11/1999 | Ashby et al. |
| 6,267,773 | B1 |  | 7/2001  | Gadberry et al. |

OTHER PUBLICATIONS

Baxter Healthcare Corp., Sales Brochure, 1994.
Pilling Catalog, 1999, p. 274.
Aesculap Catalog 1998, p. 658.
Baxter Healthcare Corp. Catalog, 1988, p. 56–58, 60.
Jarit Catalog, 2000, p. 318–320.
Applied Medical, U.S. Price List, 1999, p. 18.
Codman Surgical Products Catlog, 1996, p. C–10.

* cited by examiner

Primary Examiner—Julian W. Woo
(74) Attorney, Agent, or Firm—Morrison & Foerster LLP (57) ABSTRACT

A surgical clip with adjustable bias spring. The surgical clip includes a moveable slide assembly, whereby the positioning of the slide relative to the clip adjusts the relative compression or extension of the biasing spring.

19 Claims, 11 Drawing Sheets

SURGICAL CLIP WITH ADJUSTABLE BIASING FORCE

BACKGROUND

The present invention relates to surgical clips, more particularly surgical clips of the type typically referred to as parallel jaw clips.

Surgical clips are commonly used to occlude body conduits such as blood vessels during surgical procedures. A common type of surgical clip is the parallel jaw clip that includes a pair of jaws oriented generally parallel to one another and moveable from an open to a closed position. Many such clips include compression or extension springs for biasing the jaws together in the closed position. Representative of such clips are those described in, e.g., U.S. Pat. Nos. 3,509,882, 4,931,058, 5,653,720 and 6,267,773. Such clips have gained wide acceptance and are easy to place and remove, and provide for dependable occlusion. Such clips are also quite popular for other applications, such as suture tags, and identification markers.

While conventional parallel jaw clips have numerous advantages, they have been limited in the past in that they provide for only a single, fixed force that biases the jaws together. This is because these clips are manufactured with the compression or extension spring in a fixed, predetermined position. In turn such a clip delivers a fixed, predetermined amount of occlusive force to the target blood vessel or body conduit when the clip is deployed. In order to vary the amount then of occlusive force delivered to any given target blood vessel or body conduit, one must then select between a number of different clips, each of which may provide a different amount of occlusive force, depending on the dimensions of the clip, biasing spring, and its relative tension or compression. It would be advantageous to provide for a single adjustable clip that could provide for a variety of occlusive forces. Such a clip would provide a great deal of convenience, and minimize the number and types of clips currently prepared for typical surgeries. In addition, damage to occluded vessels caused by the use of too much occlusive force as can occur due to a tendency to err on the side of providing more rather than less occlusive force, will be mitigated due to the ability to more closely control the amount of occlusive force provided by such a clip.

SUMMARY OF THE INVENTION

The present invention meets these and other needs and provides for a surgical clip where the compression or extension of the biasing spring is adjustable, such that a single clip can be adjusted to provide for and deliver various occlusive forces. The surgical clip includes first and second jaw components having first and second body elements in telescoping relationship with one another, along with first and second jaw elements that are moveable toward and away from one another. The clip further includes a slide that is moveable along the longitudinal axis of the telescoping body elements and that is securable at two or more locations along the axis. A spring for biasing the jaws together is provided, with one end of the spring being engaged with the slide such that the relative biasing force exerted by the spring is dependent upon the location of the slide along the axis. The spring can either be a compression or extension spring, depending on the configuration of the jaw components, but in either event the degree of compressive or extensive force supplied by the spring can be adjusted by altering the position of the slide along the axis. In turn, the occlusive force provided by the clip is thus varied proportionally.

In one aspect of the invention, a surgical clip includes first and second jaw components having a first and second barrels, respectively, with the second barrel telescopically slidable within the first barrel. The first and second jaw components include first and second jaws, respectively, that extend radially from the first and second barrels, respectively, and that are moveable toward and away from one another. The first jaw component further includes a first end cap secured to the first barrel, and a slide in association with the cap, the slide being moveable between two or more fixed locations along the cap. The second jaw component includes a second end cap secured to the second barrel. A spring for biasing the jaws together in a closed position is provided, the spring residing within the barrel interiors with one end of the spring being engaged with the slide and the other end engaged with the second end cap.

In a variation of this aspect, the first end cap includes one or more guide slots for receiving the slide. The slide can further be provided with one or more arms that are received through the one or more guide slots. In a further variation of this aspect, the guide slots can also include notches extending from the guide slots and into which the slide arms are engageable. The slide arms that can be translated along the guide slots and then rotated into and engaged with the guide notches. In this manner the slide can be secured at positions defined by the notch locations.

In another aspect of the invention, a surgical clip also includes first and second jaw components having a first and second barrels, respectively, with the second barrel telescopically slidable within the first barrel. The first and second jaw components include first and second jaws, respectively, that extend radially from the first and second barrels, respectively, and that are moveable toward and away from one another. A first end cap is located on the end of the first barrel opposite the first jaw, with the first end cap being rotatable about the longitudinal axis of the barrels. A slide is disposed within the first barrel and adapted for engagement with the first end cap such that rotation of the first end cap translates the slide along the axis, with the slide further being securable at two or more spaced apart locations along the axis. The second jaw component includes a second end cap secured to the second barrel. A spring for biasing the jaws together in a closed position is also provided, the spring residing within the barrel interiors with one end of the spring being engaged with the slide and the other end engaged with the second end cap.

In a variation of this aspect, the slide can further include a cam surface oriented at an oblique angle to the longitudinal axis that is engageable with a cam pin located on the first end cap. The cam surface can further include a continuous track extending circumferentially around the cam surface with the pin engageable and securable along the track.

In yet another aspect of the invention, a surgical clip includes a slide that is configured for continuous securement along the longitudinal axis, rather than being securable in fixed, spaced apart increments. In one such variation of this aspect, the surgical clip further includes a threaded stem with slide being threaded onto the stem.

The invention also provides for methods of using surgical clips according to the invention for occluding blood vessels and body conduits and for other applications such as suture tags and identification markers.

The invention and its advantages will be even more apparent in view of the following description and accompanying drawings.

DESCRIPTION OF PREFERRED EMBODIMENTS AND MODES FOR CARRYING OUT THE INVENTION

Figure 1:
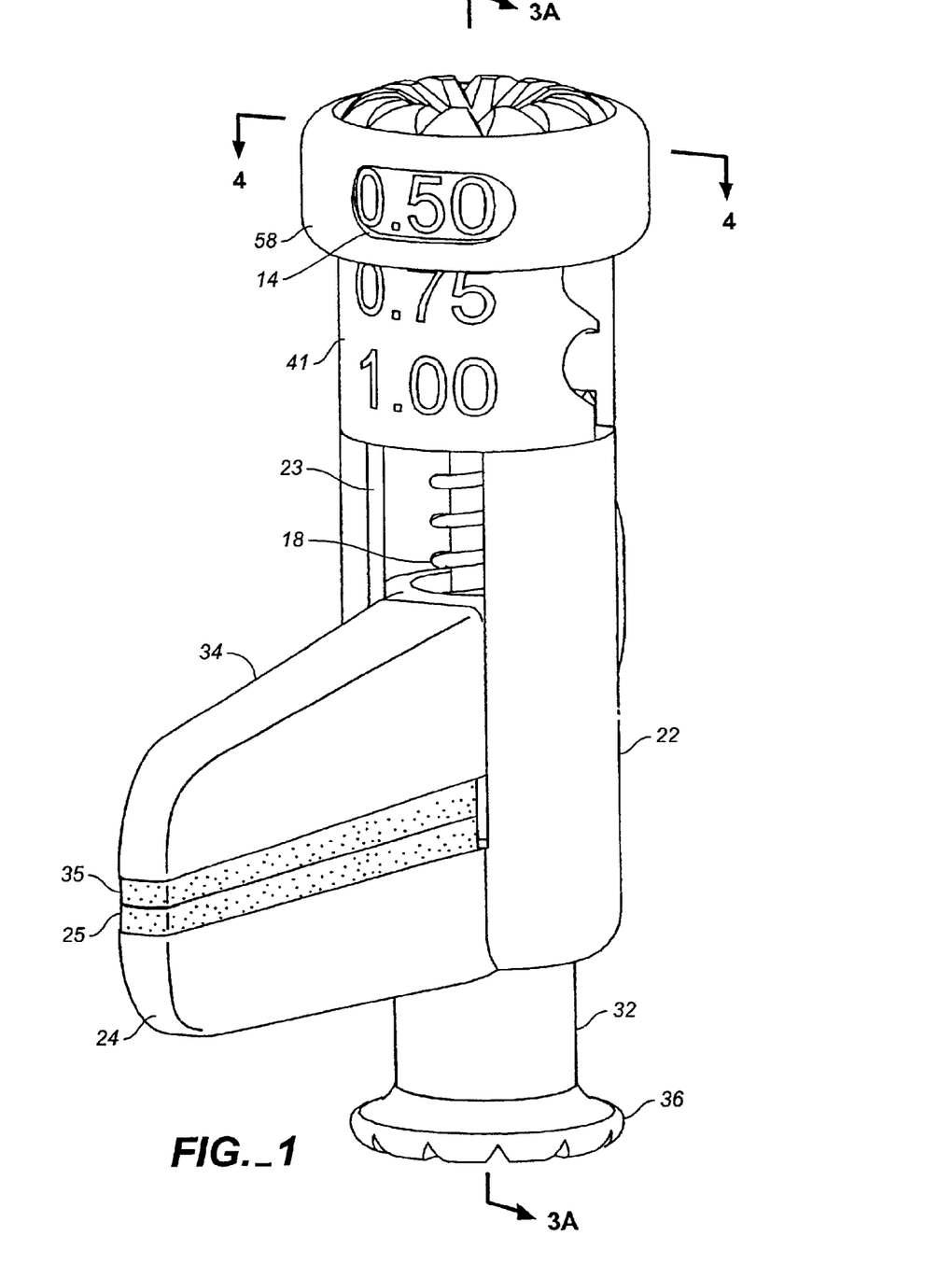
FIG. 1 is a perspective view of a surgical clip according to one embodiment of the invention.
Figure 2:
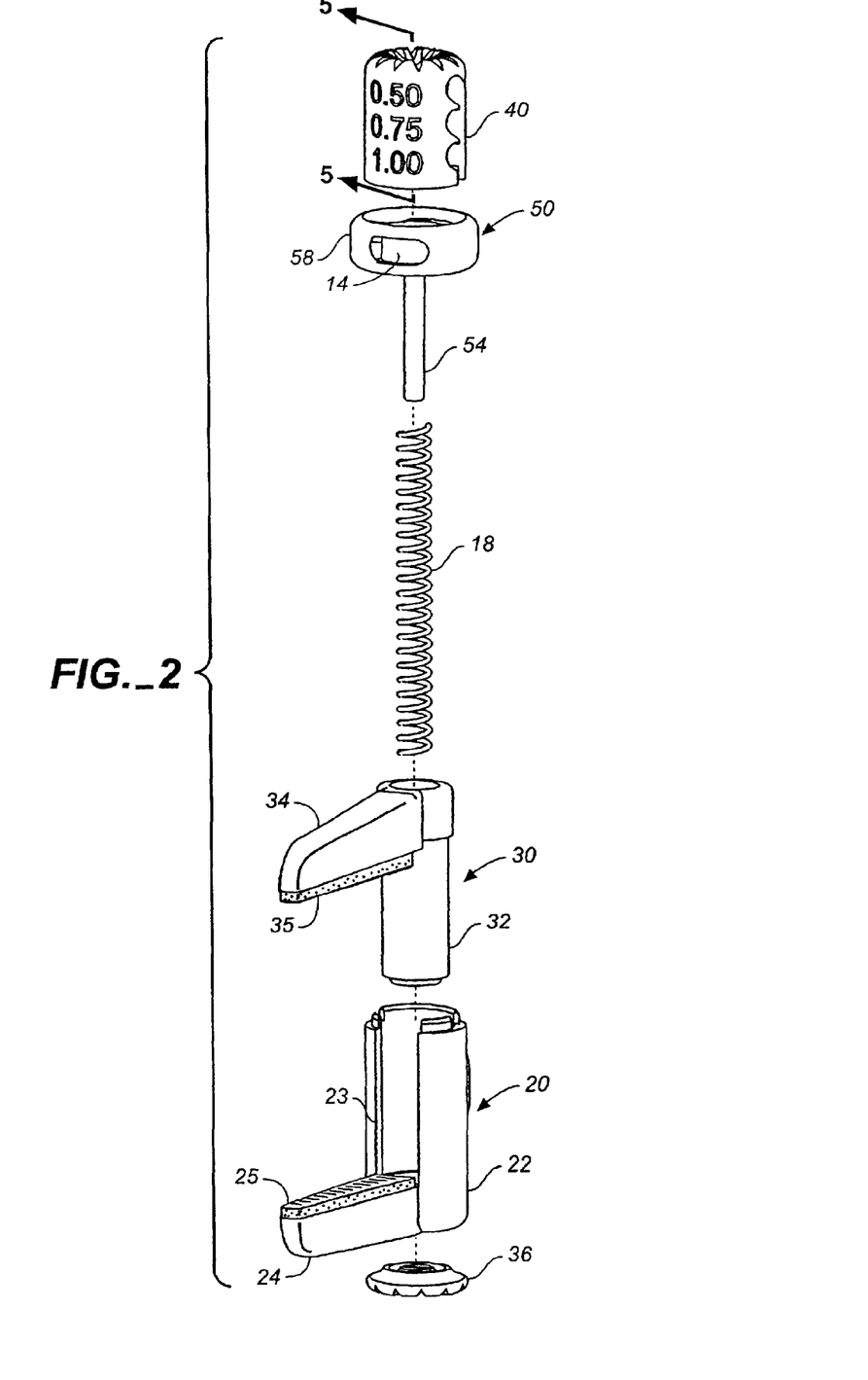
FIG. 2 is an exploded perspective view of the surgical clip of FIG. 1, showing the components of the surgical clip of FIG. 1, including the jaw, slide, spring and end cap components.
Figure 3A:
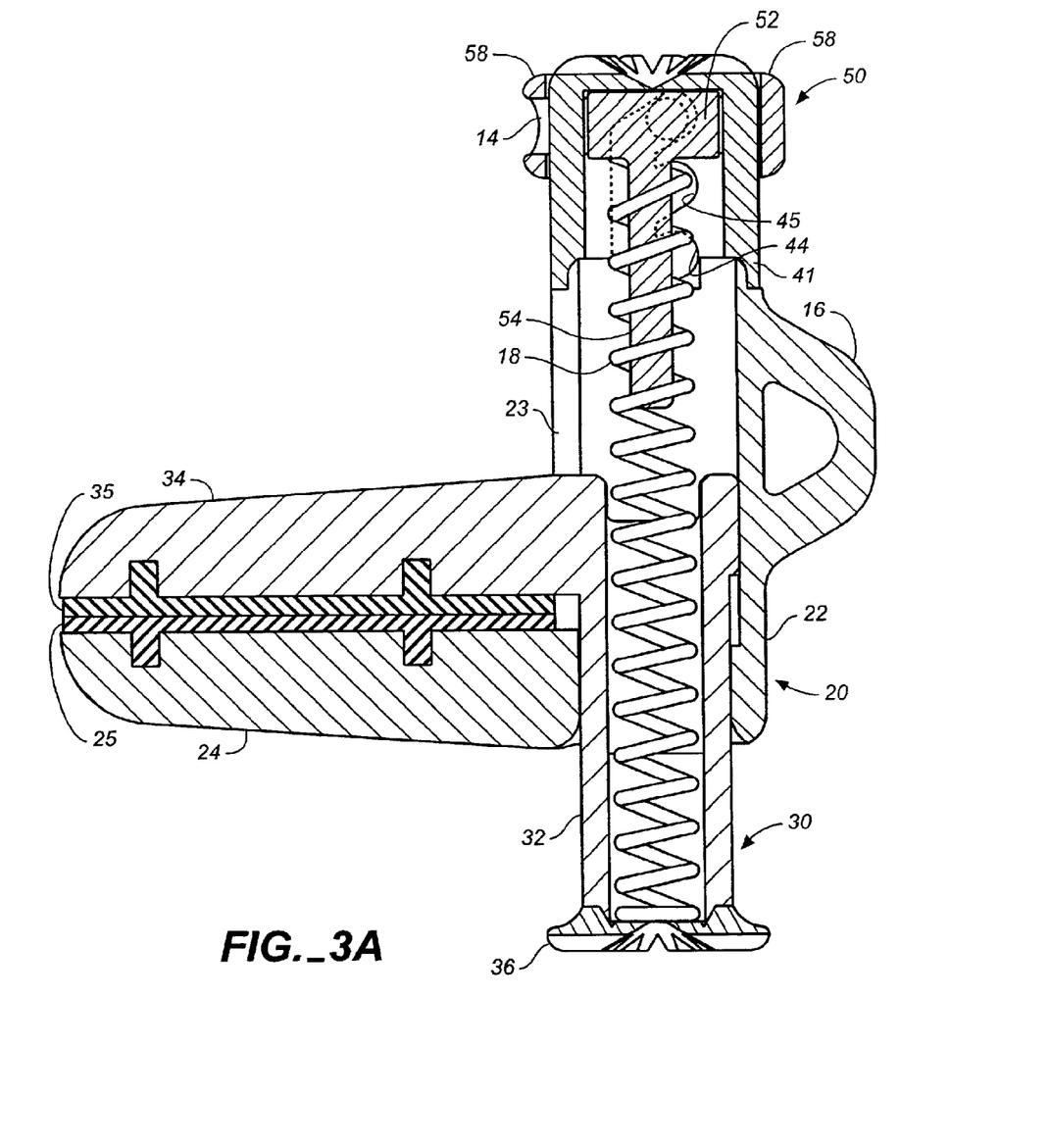
FIG. 3A is a side cross-sectional view of the surgical clip of FIG. 1, taken along the plane designated by line 3A—3A of FIG. 1, with the jaws in a closed position.
Figure 3B:
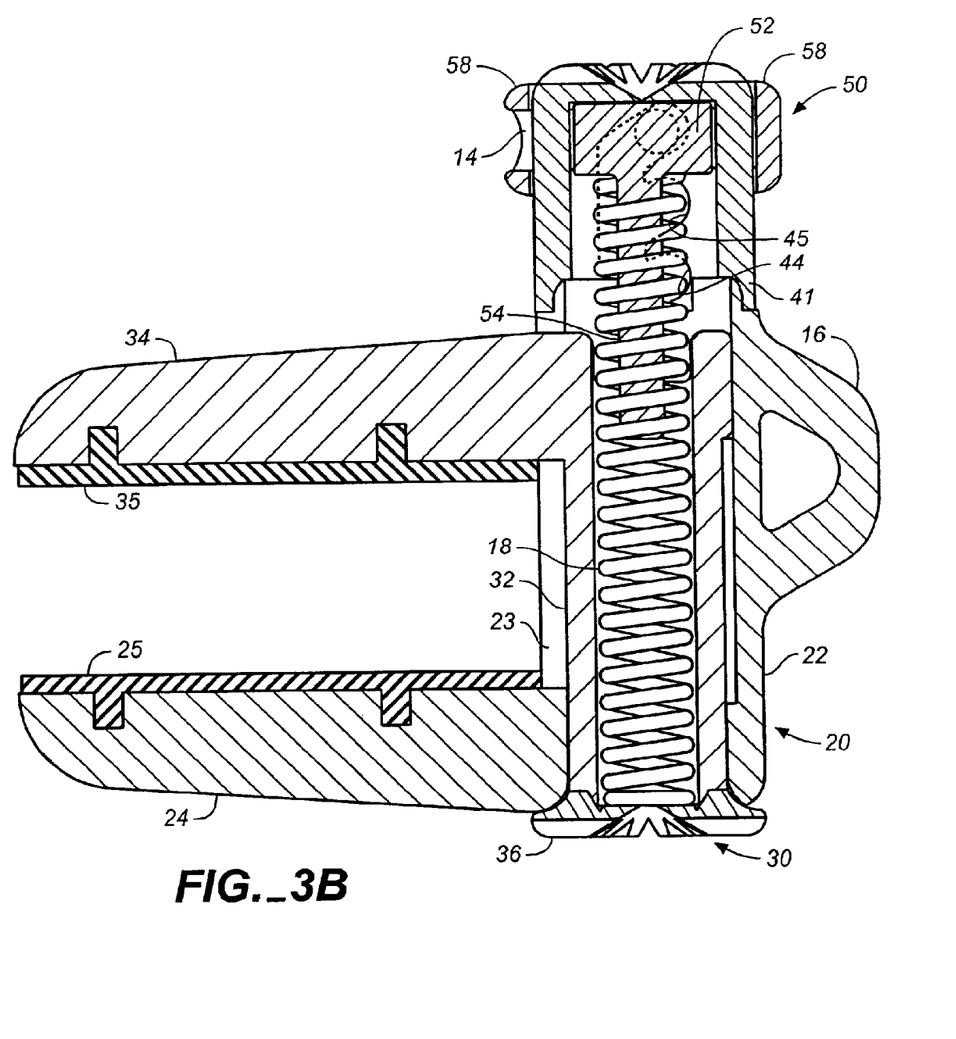
FIG. 3B is a side cross-sectional view of the surgical clip of FIG. 1, showing the jaws in an open position.

A surgical clip according to one embodiment of the present invention is depicted in FIGS. 1–3. Surgical clip 10 includes jaw components 20 and 30, which include barrels 22 and 32, respectively. Barrel 22 is generally cylindrical with a hollow interior that opens at either end. Jaw 24 extends radially from one end of barrel 22. End cap 40 is secured to the barrel at the other end of the barrel from jaw 24. Longitudinal slot 23 extends lengthwise along barrel 22 from jaw 24 to end cap 40. Barrel 32 is likewise generally cylindrical with a hollow interior, and is further proportioned for slidable receipt within barrel 22, such that barrels 32 and 22 can move in a telescoping relationship to one another. Suture tie loop 16 is provided on Barrel 22. Jaw 34 extends radially from one end of barrel 32 and is proportioned to be received and extend through longitudinal slot 23 of barrel 22. The other end of barrel 32 is closed off by the provision of end cap 36. Jaws 24 and 34 are further provided with pads 25 and 35 that offer cushioning to a clamped vessel or body conduit.

Figure 4:
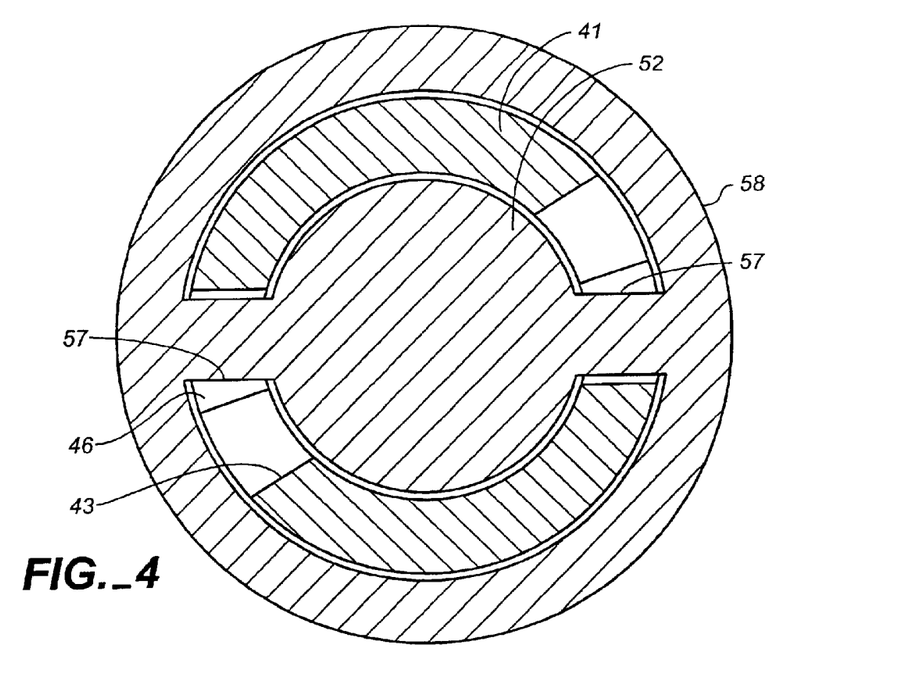
FIG. 4 is a cross-sectional view of the surgical clip of FIG. 1, taken along the plane designated by line 4—4 of FIG. 1, showing the slide component engaged with the end cap.
Figure 5:
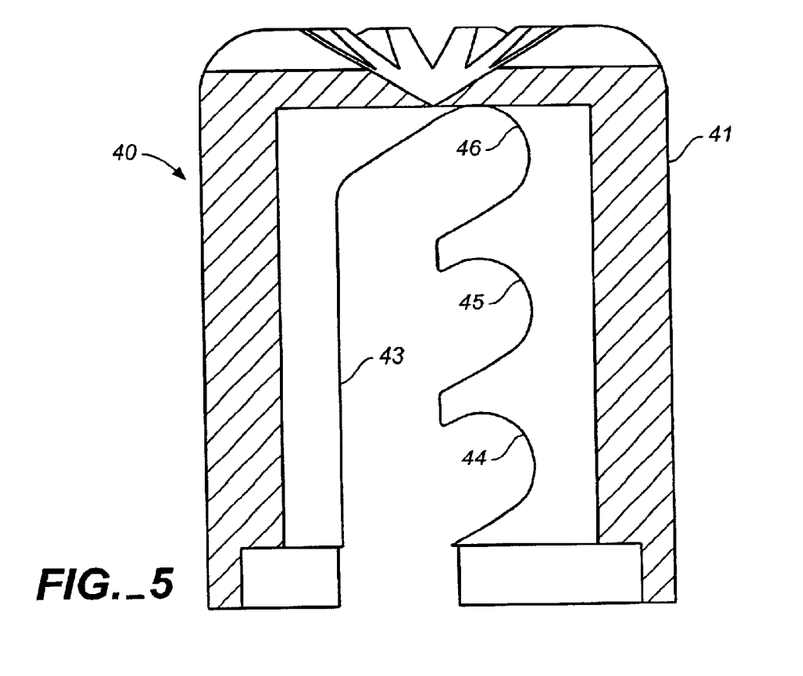
FIG. 5 is a sectional view of the end cap shown in FIG. 2, taken along the plane designated by line 5—5 of FIG. 2.

As more clearly shown in FIGS. 3–4, end cap 40 itself includes hollow cylindrical portion 41 which is configured to be generally contiguous with barrel 22. The cap includes guide slots 43 that extend lengthwise along cylindrical portion 41, with notches 44–46 extending from the guide slots. As further depicted in FIGS. 5–6, slide 50 includes body portion 52 and collar 58 connected by arm 56, 57.

Figure 6:
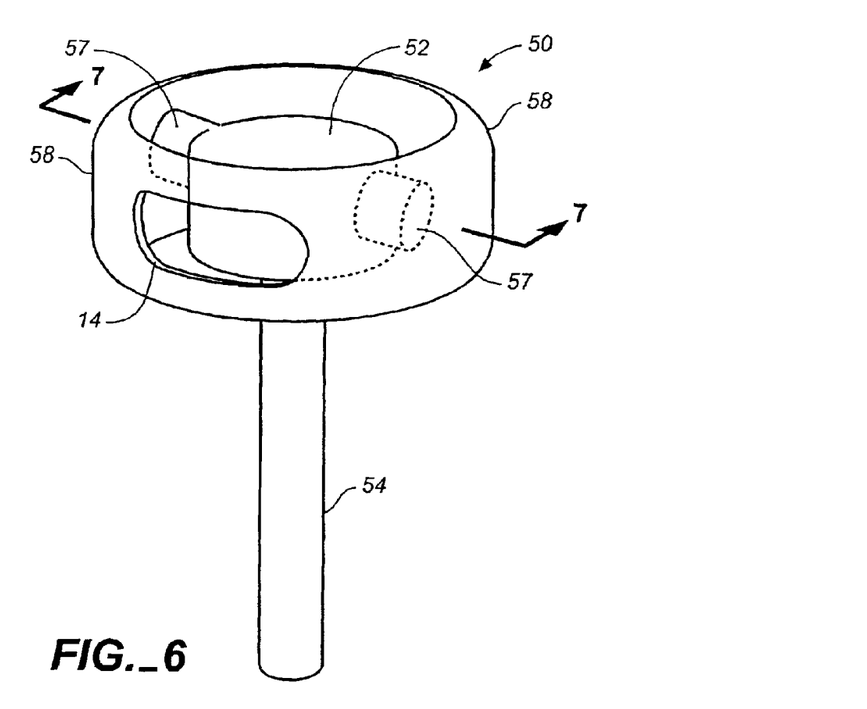
FIG. 6 is a perspective view of the slide shown in FIG. 2.
Figure 7:
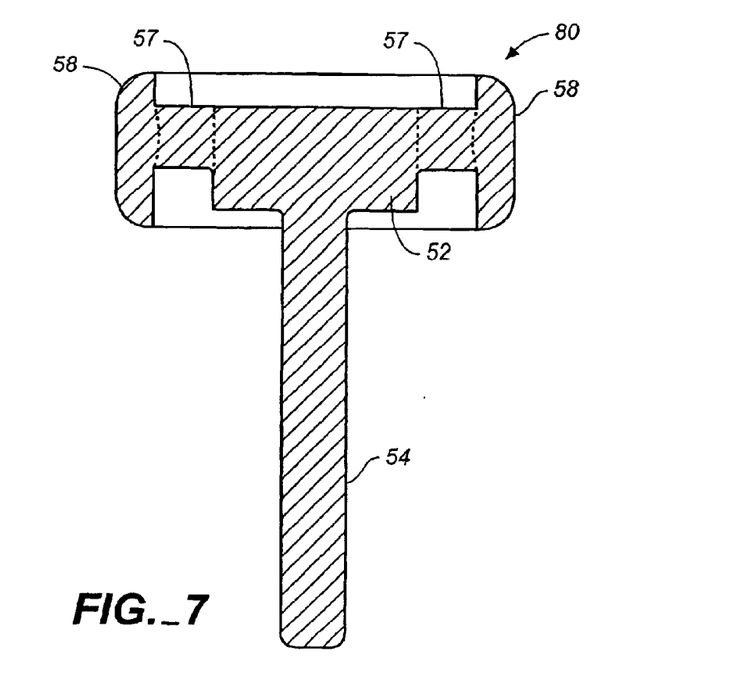
FIG. 7 is a sectional view of the slide of FIG. 6, taken along the plane designated by line 7—7 of FIG. 6.

Window cut-out 14 opens through a portion of collar 58. Body portion 52 is disc shaped with a diameter approximately that of the outer diameter of barrel 32. Collar 58 is proportioned to be slidably received over end cap 40. Arms 56 and 57 are configured for slidable receipt within guide slots 43 of end cap 40. Stem 54 extends perpendicularly from body portion 52.

Compression coil spring 18 is disposed within barrels 32 and 22 and is engaged at either end with end cap 36 and body portion 52 of slide 50. Stem 54 is configured to be received within the coil spring, to further orient and stabilize the spring. Coil spring 18 biases the jaws into the closed position, as depicted in FIG. 3A. Pressure exerted on the two end caps toward one another opens the jaws of the clip for placement onto the target vessel, as depicted in FIG. 3B.

Adjustment of slide 50 relative to end cap 40 can place the coil spring into greater or lesser compression, such that the biasing force exerted by the coil spring is increased or decreased, thereby creating a proportional increase or decrease in clamping force exerted by the jaws. Arms 56 and 57 of slide 50 are moveable along guide slots 42, 43 of end cap 40, which in turn allows for translational movement of the slide along a longitudinal axis defined by barrels 22 and 32. In order to secure the slide in a fixed position along the end cap, arms 42, 43 must be received in and engaged with one of the pairs of notches 44–46. This is accomplished by positioning the arms at the desired notch openings and then rotating the slide about the longitudinal axis until the arms are received into and engaged with the desired pair of notches. As shown in FIGS. 3–4, the arms are engaged in notch 43. In this position, the spring provides the least amount of biasing force. By moving the slide and engaging it with notches 45 or 44, the spring is placed into greater degrees of compression, and a concomitant increase in biasing force. Markings can be provided on cap 40 that are visible through window 14 of collar 58. The markings can correspond to the notch positions and thus provide a visual aid to the user indicating to what level of biasing force the clip has been adjusted. The notches extend at an angle from the guide slots, but are oriented such that upon receipt in the notches, the force of the coil spring retains the arms in the notches. In the embodiment shown, the notches are oriented at approximately 30° from normal, relative to the longitudinal axis.

Figure 8:
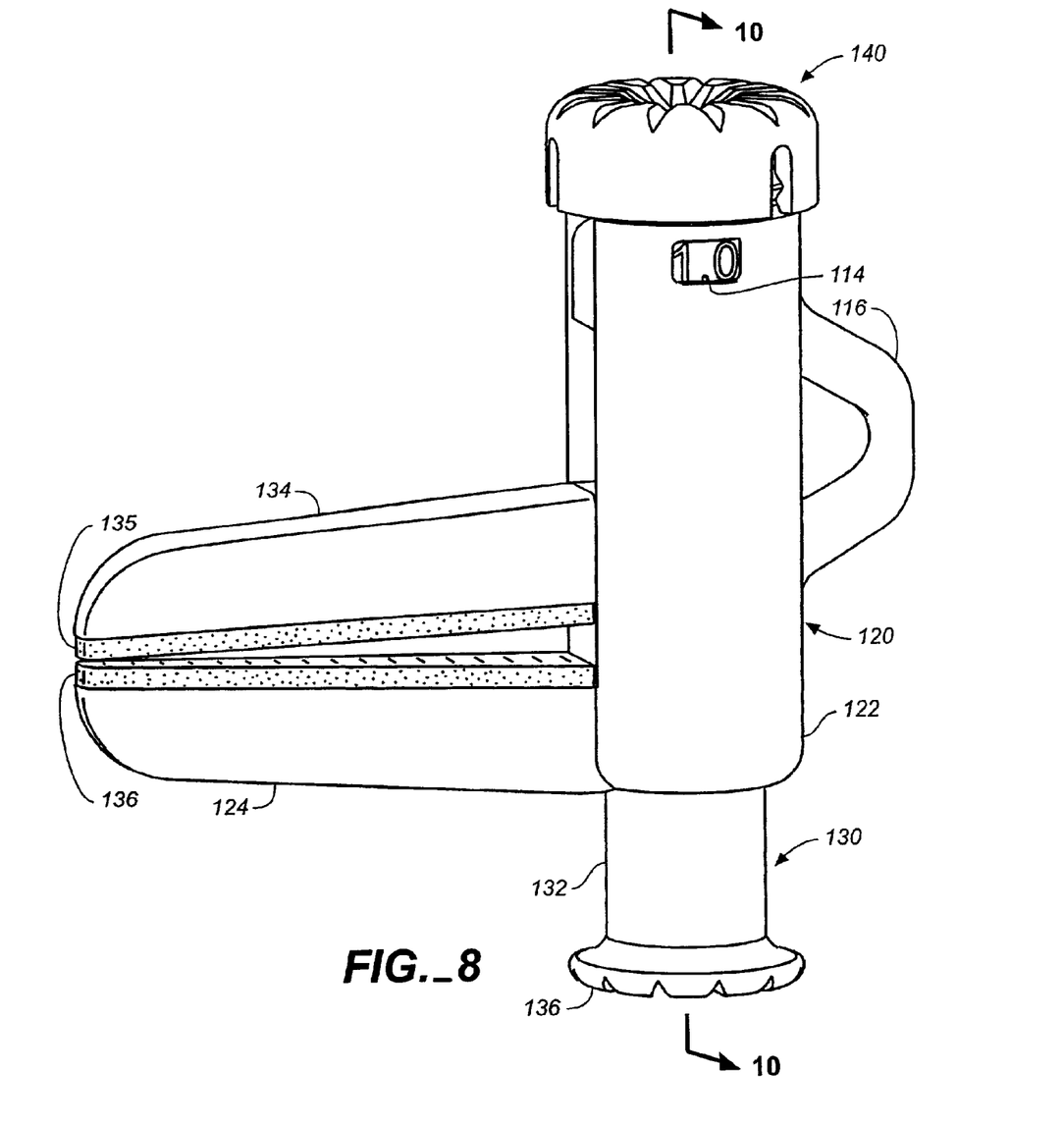
FIG. 8 is a perspective view of a surgical clip according to a second embodiment of the invention.
Figure 9:
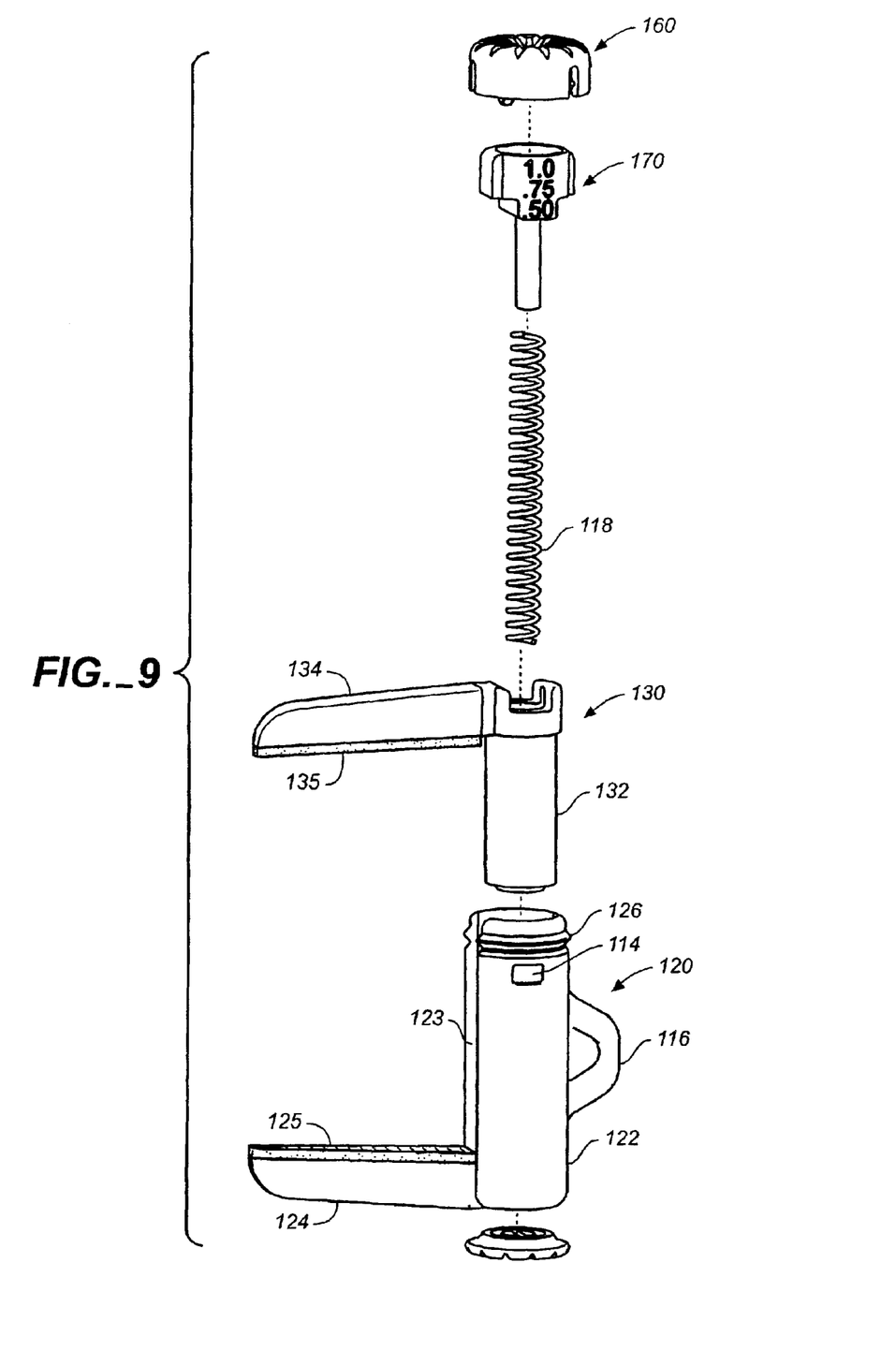
FIG. 9 is an exploded perspective view of the surgical clip of FIG. 8, showing the components of the surgical clip of FIG. 8, including the jaw, slide, spring and end cap components.
Figure 10:
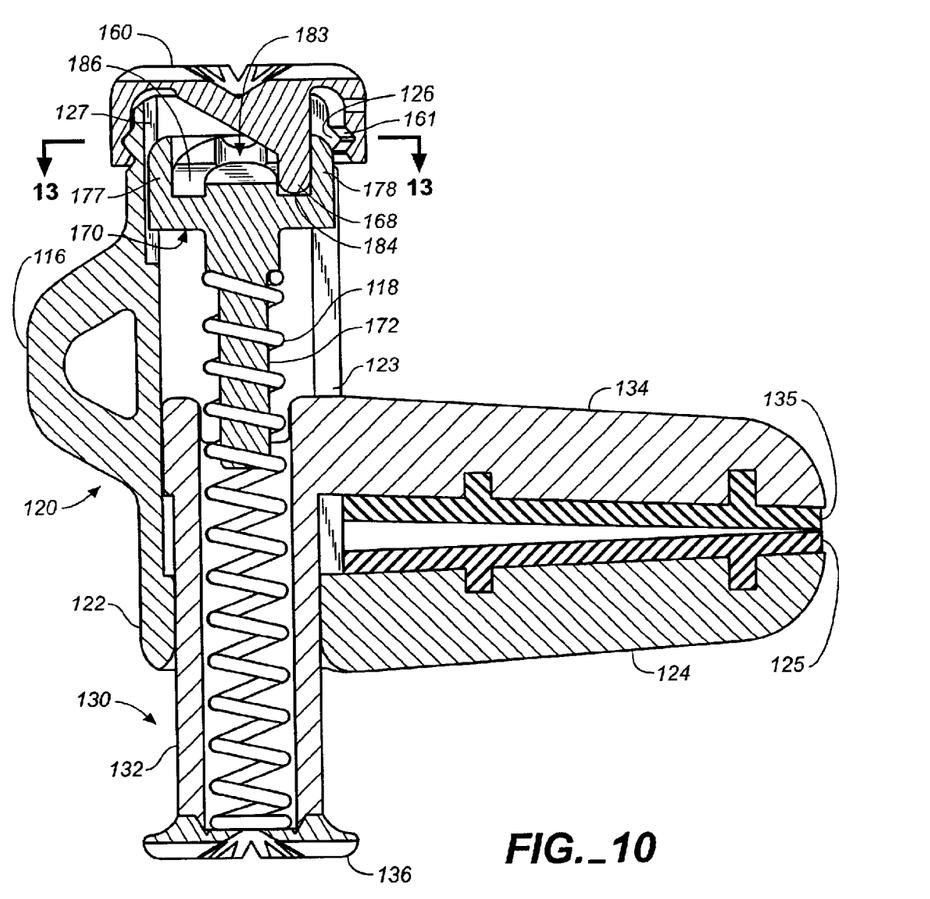
FIG. 10 is a side cross-sectional view of the surgical clip of FIG. 1, taken along the plane designated by line 10—10 of FIG. 8.

A second embodiment of the invention is depicted in FIGS. 8–10. Surgical clip 110, similar to surgical clip 10 above, includes jaw components 120 and 130 that include barrels 122 and 132, respectively. Again, barrel 122 is generally cylindrical with a hollow interior that opens at either end. Jaw 124 extends radially from one end of barrel 122, with longitudinal slot 123 extending lengthwise from the jaw to the other end of the barrel. Barrel 132 is likewise generally cylindrical with a hollow interior, and proportioned for slidable receipt within barrel 122, such that barrels 132 and 122 can move in a telescoping relationship to one another. Jaw 134 extends radially from one end of barrel 132 and is proportioned to be received and extend through longitudinal slot 123 of barrel 122. Pads 125 and 135 are provided on the jaw surfaces. End caps 160 and 136 are provided on the ends of barrels 122 and 132, respectively, opposite their respective jaws. Slide 170 and compression coil spring 118 are disposed between end caps 160 and 136, with one end of the coil spring in engagement with slide 170 and the other end in engagement with end cap 136.

Figure 11:
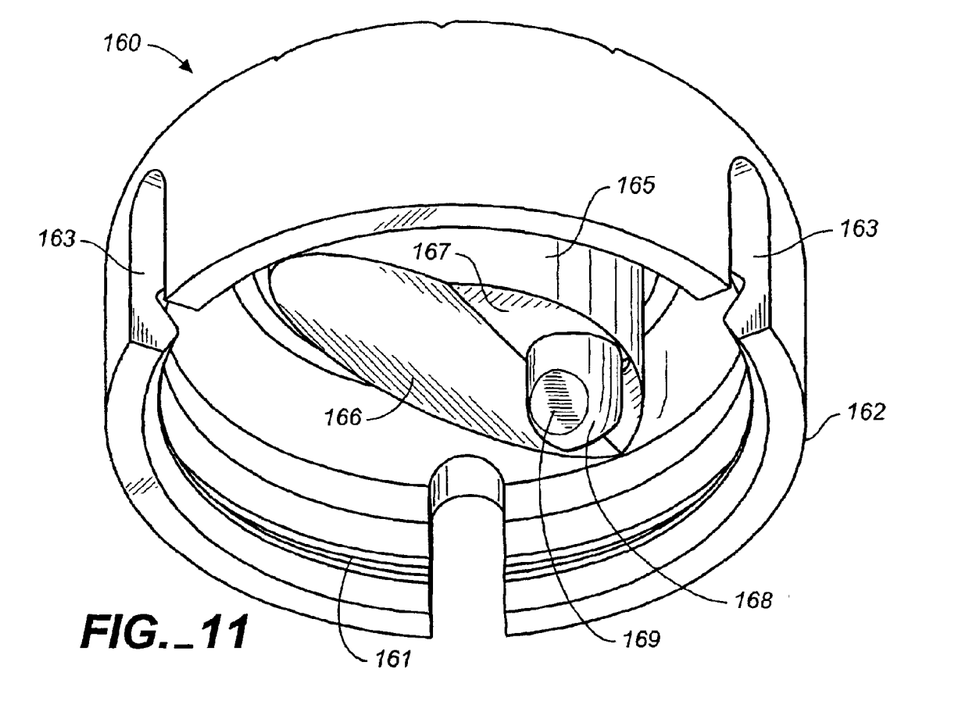
FIG. 11 is a perspective view of the end cap shown in FIG. 9.

As shown more clearly in FIGS. 10–11, end cap 140 and barrel 122 are configured to allow for rotational movement of the end cap about the end of barrel 122. Barrel 122 includes flange 126 that extends circumferentially outward from the barrel. Cap 160 includes corresponding recess 161 that extends circumferentially around the interior of rim 162 of the cap. The cap is snap fit over the end of the barrel such that the flange 126 is engaged in recess 161. The cap rim is further provided with a series of notches 163 that allow the rim to flex outwardly to aid in snapping the cap onto the barrel end. The underside of cap 160 includes body 165 that fits within barrel 122 and extends inwardly. The body 165 includes a face 166 oriented at an angle to the cap surface, and narrower flat portion 167 oriented generally parallel to the cap surface. Cam pin 168 extends from flat portion 167. The tip of cam pin 168 is generally hemispherical, but contains two facets 169 on opposing sides of the tip. The tolerances between the flange and recess, and between the barrel and the cap rim and cap body in general, are such that the cap can easily be rotated relative to the barrel. In this fashion, the cap can thus be rotated, in either direction, about the longitudinal axis defined by barrels 122 and 132.

Figure 12:
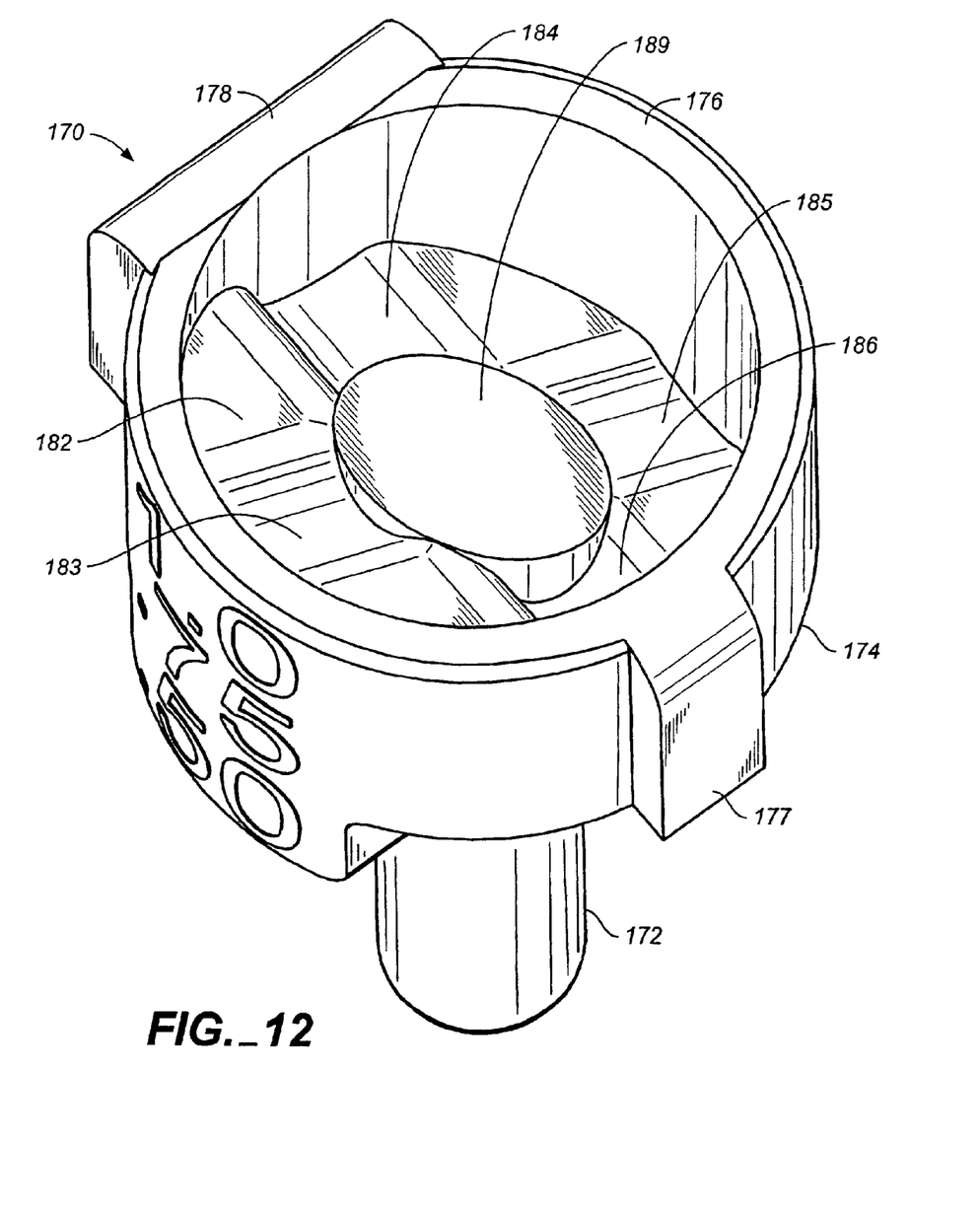
FIG. 12 is a perspective view of the slide shown in FIG. 9, with portions of the slide depicted by phantom lines.
Figure 13:
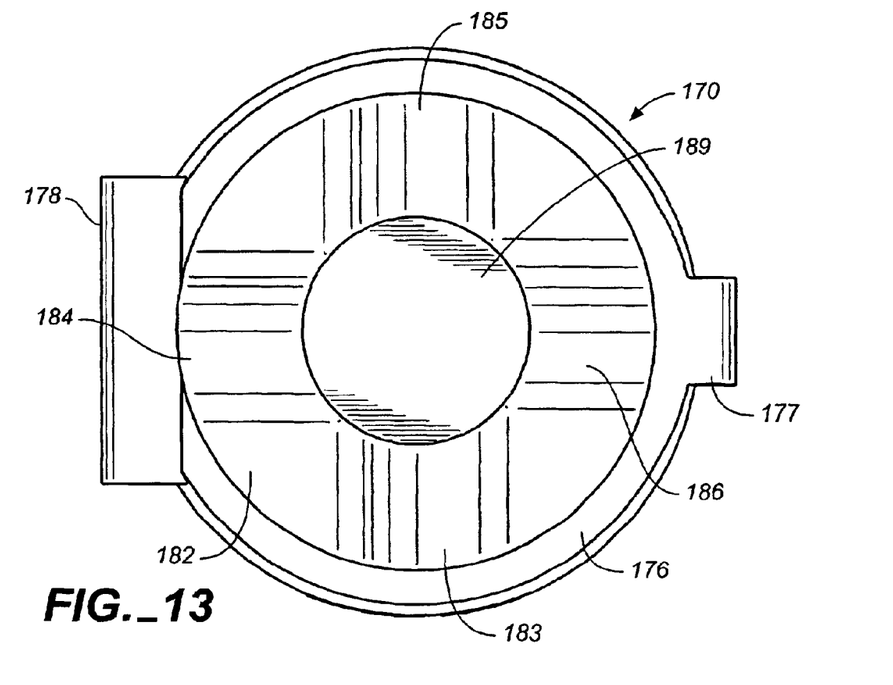
FIG. 13 is a cross-sectional view of the surgical clip of FIG. 10, taken along the plane designated by line 13—13 of FIG. 10, showing the slide positioned within the barrel of one of the jaw components; with the end cap.

As shown more clearly in FIGS. 12–13, slide 170 includes slide body 174 and slide stem 172 which extends from the slide body. Stem 172 is configured to be received within coil spring 118, with the end of coil spring engaging shoulder 173 of the stem, as seen more particularly in FIG. 10. Slide body 174 includes elongate ribs 177 and 178 that extend radially of the body. As seen more particularly in FIG. 13, rib 177 is the thinner of the two and is configured for receipt in corresponding groove 127 provided on the interior wall of barrel 122. Rib 178 is the wider of the two and is received in slot 123 of barrel 122. The provision of ribs 177, 178 and corresponding groove 127 and opening 123 allows for translational movement of the slide within barrel 122 and along the axis defined by barrels 122 and 132, but prevents rotation of the slide relative to the barrels.

Slide body 174 itself is of a generally cylindrical shape and includes side wall 176. Cam surface 189 is disposed within the slide body and is oriented on a plane that is at an oblique angle to the axis defined by barrels 122 and 132. Cam surface 189 is generally contiguous with side wall 176 at that part of the surface which is furthest away from stem 172, as seen in FIG. 12. Track 182 extends circumferentially around cam surface 189. Depressions 183–186 in the track are provided at spaced apart locations along the track, with depression 183 located at the furthest point along the track from stem 172, depression 185 located at the closest point along the track from stem 172, and depressions 184 and 186 located at mid-points along the track between depressions 183 and 185.

Once assembled, the end cap and slide operate together to form a cam mechanism which transforms rotational movement of the cap into reciprocating translational movement of the slide. The biasing force of coil spring 118 maintains slide 170 in engagement with end cap 160. More specifically, track 182 of cam surface 180 is maintained in engagement with cam pin 168 of the end cap 160, which rides along track 182 as end cap 160 is rotated. Depressions 183–186 are configured to engage and retain cam pin 168. The engagement and retention of the cam pin in the depressions is further aided by the facets 169 of pin 168, which are oriented to engage areas of the depressions near the transition of the track into the depressions. In operation, an audible click is produced when the pin engages a depression, signaling to the user that such engagement has occurred. By providing additional rotational force to the end cap, the resistance provided by the pin/depression engagement can be overcome, and the pin can be disengaged from the depression and again ride along the track.

By action of the cam mechanism provided by the end cap and slide, coil spring 118 can be placed into greater or lesser compression, such that the biasing force exerted by the coil spring is increased or decreased. This in turn provides for a proportional increase or decrease in clamping force exerted by the jaws. With cam pin 168 engaged in depression 185, the coil spring is in its least compressed state and is placed into greater compression as the cam pin is rotated about the track. The greatest compression of the coil spring is achieved with the pin engaged in depression 183. An intermediate level of compression is achieved with the pin engaged in depressions 184 or 186. The clip as shown in FIG. 10 is adjusted such that pin 168 is engaged in depression 186, providing an intermediate level of compression. Markings can be provided on the outside of sidewall 176 of the slide that align with window cut-out 114 provided on barrel 122. The markings can correspond to the positions of depressions 183–186, thereby providing a visual indication to the user as to what level of biasing force the clip has been adjusted.

The jaw components, end caps, and slide of clips 10 and 110 are formed of an easily movable plastic, such as a polycarbonate or polypropylene, that is able to withstand the forces exerted by the spring. The spring 18 or 118 itself is stainless steel or spring steel. One skilled in the art will appreciate that there are a number of suitable alternative materials known in the art that can also be used. Upon assembly, end caps 36, 40 or 136 are bonded to their respective barrels using ultrasonic welding or other similar techniques. The jaw pads offer cushioning to a clamped vessel or body conduit. The pads can be formed of an elastomer or other like material and can further be textured to improve the grip of the pad on the clamped vessel or conduit. The pads can be affixed to the jaws using mechanical bonding, insert molding, adhesives or other known means.

In addition to the above disclosed embodiments, there are many other variations which are contemplated and which will be apparent to those skilled in the art. For example, the invention also provides for adjustable spring clips which operate using a tension spring rather than a compression spring to bias the jaws together. In one such embodiment (not shown) the clip includes telescoping barrels configured such that a coil tension spring operates to draw the barrels together. The jaws are oriented on the barrels such that they are likewise biased together in a closed position as the barrels themselves are drawn together. An example of a parallel jaw clip that operates according to this principle is described in U.S. Pat. No. 5,984,934, which is incorporated herein by reference in its entirety. Accordingly, a tension spring can be secured at one end to the fixed end cap of one barrel and at the other end to the slide body of a slide/end cap assembly, similar to that of end cap 40 and slide 50 of surgical clip 10 previously described above. The tension imparted by the spring to bias the jaws together, and by extension the occlusive force provided by the jaws themselves, again is adjustable, and depends on the position of the slide relative to the end cap. In such an embodiment, the end cap can again be provided with guide slots and notches where the notches are again angled from the guides slots. However, the notches are oriented such that the force of the spring pulls the guide slot arms into the desired pair of notches when the slide is positioned at the desired pair of notches and rotated.

The above described clips are especially suitable for use in laproscopic situations. Preferably, for laproscopic use, the height of the clip in its closed state is such that it can be accommodated through a trocar or other common laproscopic device. Such clips can be further configured with actuation tabs that can be manipulated by clip applier.

Other variations on the invention provide for alternative mechanisms for adjusting the spring tension or compression levels. For example, the adjustment mechanism offered by end cap 40 and slide 50 of clip 10 provides for incremental adjustments, i.e., in increments from one notch pair to the next. Similarly, the cam mechanism of end cap 160 and slide 170 likewise provides for incremental adjustments from one depression to the next. In alternative embodiments, the slide adjustment assembly can be configured to provide for continuous adjustment of spring tension or compression levels. In one such embodiment, the slide body can be threaded onto a stem that extends from an end cap or barrel. The position of the slide body can then be adjusted by screwing the slide body to the desired position along the stem. A variety of means can be employed to allow for such adjustment. For example, the end cap or barrel itself can contain opposing indentations with cut-out slots that allow opposing portions of the slide body to extend from the end cap or barrel. These portions can be manually gripped and twisted to turn the slide body to the desired direction along the stem.

One skilled in the art will appreciate that many other modifications may be made to the embodiments described above without departing from the spirit and scope of the invention. The invention therefore is not intended to be limited to the specifics of the embodiments herein illustrated and described but rather is defined by the accompanying claims.

We claim:

1. A surgical clip comprising:
    a first jaw component having a first body element and a first jaw element extending therefrom;
    a second jaw component having a second body element and second jaw element extending therefrom, the second body element being in a telescoping relationship with the first body element, and the first and second jaw elements being moveable toward and away from one another;
    a slide moveable along a longitudinal axis defined by the first and second body elements, the slide being securable at two or more locations along the axis; and
    a spring for biasing the first and second jaws together in a closed position, the spring being engaged at one end with the slide such that the relative biasing force exerted by the spring is dependent upon the location of the slide along the axis.

2. The surgical clip of claim 1 wherein the slide is securable at predetermined fixed locations along the axis.

3. The surgical clip of claim 1 wherein the slide is rotatable about the axis.

4. The surgical clip of claim 1 further comprising a threaded stem with the slide threaded onto the stem, the stem being oriented along the axis and fixed relative to either the first or second body element.

5. The surgical clip of claim 1 wherein the first and second body elements comprise inner and an outer barrels, the inner barrel telescopically slidable within the outer barrel.

6. The surgical clip of claim 1 wherein the spring is in compression.

7. The surgical clip of claim 1 wherein the spring is in tension.

8. A surgical clip comprising:
    a first jaw component having a first barrel, a first jaw extending radially from one end of the first barrel, and a longitudinal slot extending from the first jaw;
    a second jaw component having a second barrel, and a second jaw extending radially from one end of the second barrel and through the longitudinal slot of the first barrel, the second barrel telescopically slidable within the first barrel, and the first and second jaws being moveable toward and away from one another;
    a first end cap located on the end the first barrel opposite the first jaw, the first end cap having guide slots;
    a slide disposed within the first end cap, the slide being moveable along the guide slots and securable at two or more spaced apart locations along the guide slots;
    a second end cap at the end of the second barrel opposite the second jaw; and
    a spring for biasing the first and second jaws together in a closed position, the spring residing within the barrel interiors and engaged at one end with the slide and at the other end with the second end cap.

9. The surgical clip of claim 8 wherein the guide slots are aligned parallel to a longitudinal axis defined by the first and second barrels.

10. The surgical clip of claim 9 wherein the cap further comprises two or more notches extending from the one or more guide slots.

11. The surgical clip of claim 10 wherein the slide can be engaged in the two or more notches extending from the one or more guide slots, thereby securing the slide.

12. The surgical clip of claim 11 wherein the slide can engage the two or more notches by rotational movement of the slide about the longitudinal axis.

13. The surgical clip of claim 12 wherein the slide further comprises a slide body having one or more arms extending therefrom and a collar extending from the one or more arms, the slide arms being received through the one or more guide slots, with the collar extending around the cap.

14. A surgical clip comprising:
    a first jaw component having a first barrel, a first jaw extending radially from one end of the first barrel, and a longitudinal slot extending from the first jaw;
    a second jaw component having a second barrel, and a second jaw extending radially from one end of the second barrel and through the longitudinal slot of the first barrel, the second barrel telescopically slidable within the first barrel, and the first and second jaws being moveable toward and away from one another;
    a first end cap located on the end the first barrel opposite the first jaw, the first end cap being rotatable about a longitudinal axis defined by the first and second barrels;
    a slide disposed within the first barrel, the slide adapted for engagement with the first end cap such that rotation of the first end cap translates the slide along the axis, the slide further being securable at two or more spaced apart locations along the axis;
    a second end cap at the end of the second barrel opposite the second jaw; and
    a spring for biasing the first and second jaws together in a closed position, the spring residing within the barrel interiors and engaged at one end with the slide and at the other end with the second end cap.

15. The surgical clip of claim 14 wherein the slide further includes a rib extending longitudinally of the slide that is slidably received in a corresponding slot on the first barrel.

16. The surgical clip of claim 14 wherein the slide further includes a cam surface oriented at an oblique angle to the axis, and wherein the first end cap further includes a cam pin engageable with the cam surface.

17. The surgical clip of claim 16 wherein the cam surface further includes a continuous track extending circumferentially around the cam surface, the cam pin being engageable along the track.

18. The surgical clip of claim 17 wherein the track further includes two or more spaced apart depressions that can receive and engage the cam pin.

19. A method of occluding a vessel or other body conduit using the surgical clip of any one of claims 1–18 comprising applying said surgical clip to said vessel or other body conduit.

* * * * *